(12) United States Patent
Russell

(10) Patent No.: US 9,237,848 B2
(45) Date of Patent: Jan. 19, 2016

(54) MODULAR PHYSIOLOGICAL SENSING PATCH

(71) Applicant: COVIDIEN LP, Mansfield, MA (US)

(72) Inventor: Brian Keith Russell, Annapolis, MD (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/633,896

(22) Filed: Feb. 27, 2015

(65) Prior Publication Data

US 2015/0164325 A1  Jun. 18, 2015

Related U.S. Application Data

(63) Continuation of application No. 14/495,262, filed on Sep. 24, 2014.

(60) Provisional application No. 61/883,689, filed on Sep. 27, 2013.

(51) Int. Cl.
*A61B 5/0408* (2006.01)
*A61B 5/00* (2006.01)
*A61B 5/08* (2006.01)

(52) U.S. Cl.
CPC ............. *A61B 5/0022* (2013.01); *A61B 5/0408* (2013.01); *A61B 5/04085* (2013.01); *A61B 5/08* (2013.01); *A61B 5/688* (2013.01); *A61B 5/6832* (2013.01); *A61B 5/6833* (2013.01)

(58) Field of Classification Search
CPC .................................................. A61B 5/04085
USPC .................................................. 600/391–393
See application file for complete search history.

(56) References Cited

U.S. PATENT DOCUMENTS

| | | | |
|---|---|---|---|
| 4,827,939 A | 5/1989 | Cartmell et al. | |
| 6,881,191 B2 * | 4/2005 | Oakley et al. | 600/483 |
| 8,332,009 B2 * | 12/2012 | McLaughlin et al. | 600/372 |
| 8,538,503 B2 * | 9/2013 | Kumar et al. | 600/391 |
| 2006/0030781 A1 | 2/2006 | Shennib | |
| 2006/0155183 A1 | 7/2006 | Kroecker et al. | |
| 2007/0270678 A1 * | 11/2007 | Fadem et al. | 600/372 |
| 2008/0139953 A1 * | 6/2008 | Baker et al. | 600/509 |
| 2008/0288026 A1 * | 11/2008 | Cross et al. | 607/60 |
| 2009/0076340 A1 | 3/2009 | Libbus et al. | |
| 2011/0066013 A1 | 3/2011 | Harrold | |

(Continued)

FOREIGN PATENT DOCUMENTS

WO   2012015768 A2   2/2012

OTHER PUBLICATIONS

International Search Report of International Application No. PCT/US2014/057473 dated Jan. 9, 2015.

(Continued)

*Primary Examiner* — Lee S Cohen

(57) ABSTRACT

A modular holder or patch is described that may be used with or as part of a wireless physiological sensing device. The wireless physiological sensing device may include a holder or patch, first and second electrodes, and an electronics package that may be removably coupled with the holder or patch and which may be in electrical contact with the first and second electrodes. The electronics package may include a housing, a wireless transceiver and electronic circuitry configured to process signals received via the first and second electrodes and the wireless transceiver.

20 Claims, 11 Drawing Sheets

(56) References Cited

U.S. PATENT DOCUMENTS

| | | |
|---|---|---|
| 2011/0224557 A1 | 9/2011 | Banet et al. |
| 2012/0101396 A1 | 4/2012 | Solosko et al. |
| 2012/0310070 A1* | 12/2012 | Kumar et al. ............ 600/391 |
| 2013/0116533 A1* | 5/2013 | Lian et al. ............... 600/391 |
| 2013/0116534 A1* | 5/2013 | Woo ........................ 600/391 |
| 2013/0131484 A1* | 5/2013 | Pernu et al. ............. 600/388 |
| 2014/0031663 A1* | 1/2014 | Gallego et al. .......... 600/386 |
| 2014/0100432 A1* | 4/2014 | Golda et al. ............. 600/301 |
| 2014/0275932 A1* | 9/2014 | Zadig ...................... 600/391 |

OTHER PUBLICATIONS

International Search Report of International Application No. PCT/US2014/057472 dated Jan. 9, 2015.

* cited by examiner

MODULAR PHYSIOLOGICAL SENSING PATCH

CROSS-REFERENCE TO RELATED APPLICATIONS

This application is a continuation of U.S. patent application Ser. No. 14/495,262, titled "MODULAR PHYSIOLOGICAL SENSING PATCH," filed Sep. 24, 2014, which claims priority to U.S. Provisional Patent Application No. 61/883,689, titled "MODULAR PHYSIOLOGICAL SENSING PATCH" filed on Sep. 27, 2013, each of which is incorporated by reference herein.

TECHNICAL FIELD

The present disclosure relates generally to physiological monitoring systems, and more particularly to sensor devices for remote physiological monitoring systems.

BACKGROUND

Existing methods for remotely monitoring physiological parameters of a person typically include the use of cumbersome sensors and/or wires that may limit the effectiveness of measuring active individuals. More recent wireless communications solutions may still include external wires that may easily be tangled and bulky electronics packages, rendering the sensor devices uncomfortable and/or difficult for a user. Additionally, sensor devices designed to be worn or attached to an individual may include electronics packages that have been personalized for the user. These sensor devices, with their personalized electronics, may require battery power. Yet, charging or replacing the batteries in these devices may also be difficult and may even require a user to have two different personalized sensor devices so that a replacement can be worn while the other sensor device is being charged.

Accordingly, a practitioner and patient may benefit from use of a wireless sensing device having a modular holder or patch to which the wireless sensing device may be securely attached.

SUMMARY

The described features generally relate to a modular holder or patch that may be used with or as part of a wireless physiological sensing device, as well as methods for using the same. The wireless physiological sensing device may include a holder or patch, first and second electrodes, and an electronics package that may be removably coupled with the holder and which may be in electrical contact with the first and second electrodes via the holder or patch. The electronics package may include a housing, a wireless transceiver and electronic circuitry configured to process signals received via the first and second electrodes and the wireless transceiver and to store data and processed signals.

The holder or patch may, in some embodiments, be disposable. In some embodiments, the first and second electrodes may also be disposable and may be either coupled to the holder or patch or may be integrally formed with the holder or patch. In other embodiments, the holder or patch may include a battery which may be either rechargeable or disposable. In this way, the electronics package, which may be personalized for a use by a user, may thus be removed from disposable and/or less expensive elements of the wireless physiological sensing device and then reinserted into a replacement holder or patch, requiring minimal effort by either the practitioner or the patient.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Physiological monitoring of a patient in a clinical-type setting typically includes attaching various sensing devices to the patient. In a clinical setting, the sensing devices may be attached by trained practitioners. Nevertheless, demands on time and resources may compel a practitioner to have a preference for easy-to-use and maintain sensing devices that can be attached to a patient with a minimal amount of effort and complexity. Additionally, in non-clinical settings, untrained individuals may also be expected to attach or replace already attached sensing devices. If the process for attaching or replacing a physiological sensing device is too complex, the untrained patients or other individuals may simply forego use of the physiological sensing devices.

For example, a wireless physiological sensing device may typically include electronic components that may require a battery in order to operate. In many instances, the battery supplying power to the wireless physiological sensing device may exhaust itself before the patient's use of the wireless physiological sensing device has been completed. Thus, there may be a need to replace the wireless physiological sensing device, replace the battery of the sensing device, or at least recharge the batter of the sensing device. Replacement of the entire wireless physiological sensing device can be prohibitively expensive for many patients, while replacing the battery of the sensing device may require a level of dexterity or complexity with which a patient may not be comfortable. Alternatively, recharging a battery may also require removing a battery for charging, or charging the entire wireless physiological sensing device, thus requiring either a second device or at least a second battery that may need to be inserted into the sensing device. Each instance makes demands of patients that may ultimately result in less than ideal use of the wireless physiological sensing devices. These concerns are compounded when the electronics of the wireless physiological sensing device have been customized for use by the patient.

Therefore, use of a physiological sensing device that includes a modular holder or patch may be beneficial. A separate and removable electronics package (that may be customized) may be used in conjunction with a modular holder or patch that may be easily removed and/or attached to a patient when desired. Some components of the wireless physiological sensing device may be disposable so as to minimize complexity for a patient or practitioner, while other components of the sensing device may be easily removed and reconnected to replacement components, as explained in greater detail below.

Figure 1:
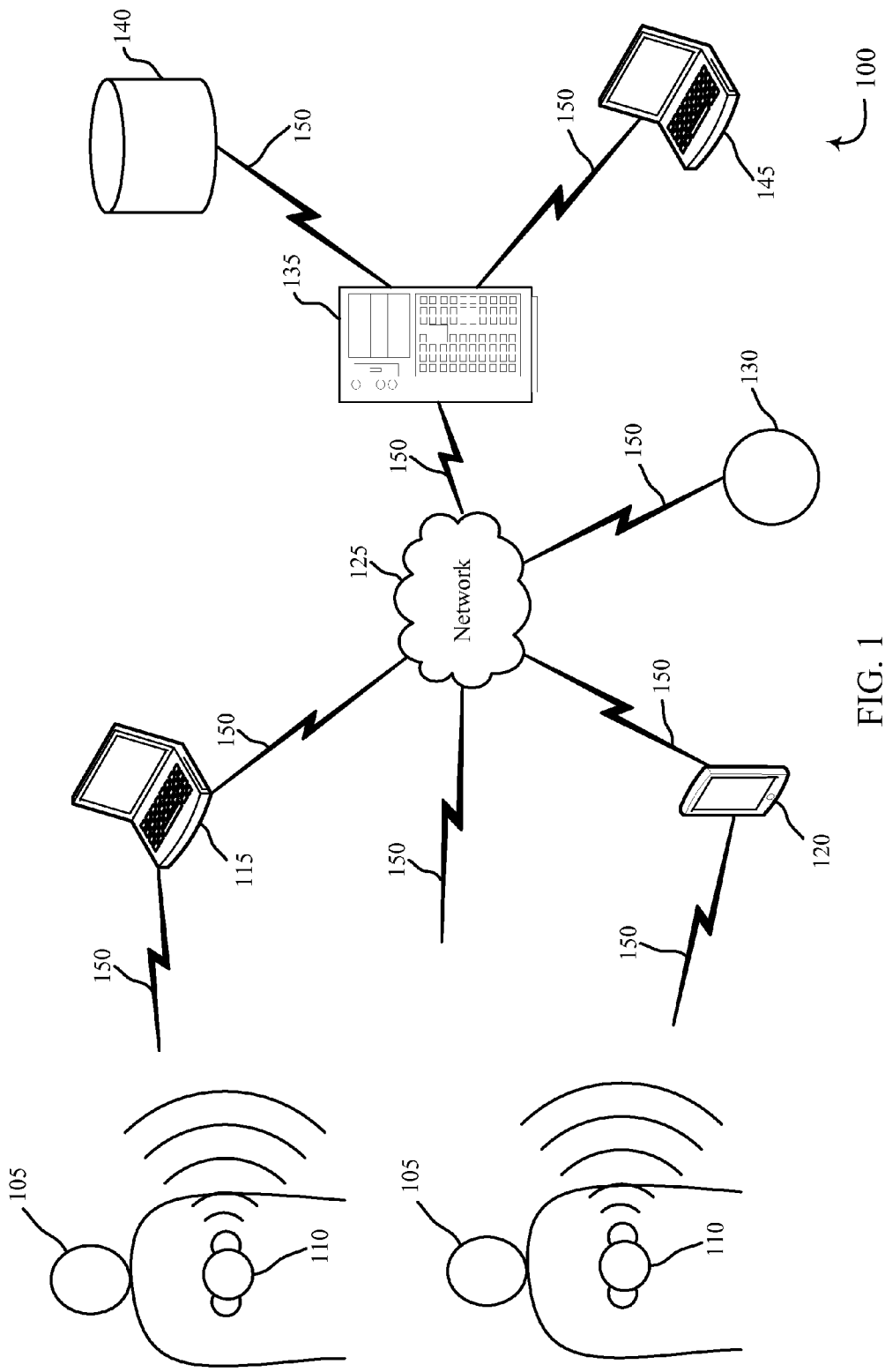
FIG. 1 is a system diagram of an example of a remote physiological parameter monitoring system.

Referring first to FIG. 1, a diagram illustrates an example of a remote physiological parameter monitoring system 100. The system 100 includes persons 105, each wearing a sensor unit 110 that may be an example of the wireless physiological sensing devices generally described above. The sensor units 110 transmit signals via wireless communication links 150. The transmitted signals may be transmitted to local computing devices 115, 120. Local computer device 115 may be a local care-giver's station, for example. Local computer device 120 may be a mobile device, for example. The local computing devices 115, 120 may be in communication with a server 135 via network 125. The sensor units 110 may also communicate directly with the server 135 via the network 125. Additional, third-party sensors 130 may also communicate directly with the server 135 via the network 125. The server 135 may be in further communication with a remote computer device 145, thus allowing a care-giver to remotely monitor the persons 105. The server 135 may also be in communication with various medical databases 140 where the collected data may be stored.

The sensor units 110 are described in greater detail below. Each sensor unit 110, however, is capable of sensing multiple physiological parameters. Thus, the sensor units 110 may each include multiple sensors such as heart rate and ECG sensors, respiratory rate sensors, and accelerometers. For example, a first sensor in a sensor unit 110 may be an accelerometer operable to detect a user's posture and/or activity level. In such an embodiment, the first sensor may be operable to determine whether the user is standing, sitting, laying down, and/or engaged in physical activity, such as running A second sensor within a sensor unit 110 may be operable to detect a second physiological parameter. For example, the second sensor may be an electrocardiogram (ECG) sensing module, a breathing rate sensing module, and/or any other suitable module for monitoring any suitable physiological parameter. The data collected by the sensor units 110 may be wirelessly conveyed to either the local computer devices 115, 120 or to the remote computer device 145 (via the network 125 and server 135). Data transmission may occur via, for example, frequencies appropriate for a personal area network (such as Bluetooth, WiFi, cellular or IR communications) or near-field or local or wide area network frequencies such as radio frequencies specified by the IEEE 802.15.4 standard or medical body area network (MBAN) frequencies specifically allocated for medical devices. In some embodiments, the sensor units 110 may also include a human-readable display or a local alert function, and may include an LED, a haptic motor, a buzzer, etc., that may serve as a local alert.

The local computer devices 115, 120 may enable the person 105 and/or a local care-giver to monitor the collected physiological data. For example, the local computer devices 115, 120 may be operable to present data collected from sensor units 110 in a human-readable format. For example, the received data may be output as a display on a computer or a mobile device. The local computer devices 115, 120 may include a processor that may be operable to present data received from the sensor units 110 in a visual format. The local computer devices 115, 120 may also output data and/or alerts in an audible format using, for example, a speaker.

The local computer devices 115, 120 may be custom computing entities configured to interact with the sensor units 110. In some embodiments, the local computer devices 115, 120 and the sensor units 110 may be portions of a single sensing unit operable to sense and display physiological parameters. In another embodiment, the local computer devices 115, 120 may be general purpose computing entities such as a personal computing device, such as a desktop computer, a laptop computer, a netbook, a tablet personal computer (PC), an iPod®, an iPad®, a smart phone (e.g., an iPhone®, an Android® phone, a Blackberry®, a Windows® phone, etc.), a mobile phone, a personal digital assistant (PDA), and/or any other suitable device operable to send and receive signals, store and retrieve data, and/or execute modules.

The local computer devices 115, 120 may include memory, a processor, an output, and a communication module. The processor may be a general purpose processor, a Field Programmable Gate Array (FPGA), an Application Specific Integrated Circuit (ASIC), a Digital Signal Processor (DSP), and/or the like. The processor may be configured to retrieve data from and/or write data to the memory. The memory may be, for example, a random access memory (RAM), a memory buffer, a hard drive, a database, an erasable programmable read only memory (EPROM), an electrically erasable programmable read only memory (EEPROM), a read only memory (ROM), a flash memory, a hard disk, a floppy disk, cloud storage, and/or so forth. In some embodiments, the local computer devices 115, 120 may include one or more hardware-based modules (e.g., DSP, FPGA, ASIC) and/or software-based modules (e.g., a module of computer code stored at the memory and executed at the processor, a set of processor-readable instructions that may be stored at the memory and executed at the processor) associated with executing an application, such as, for example, receiving and displaying data from sensor units 110.

The processor of the local computer devices 115, 120 may be operated to control operation of the output of the local computer devices 115, 120. The output may be a television, a liquid crystal display (LCD) monitor, a cathode ray tube (CRT) monitor, speaker, tactile output device, and/or the like. In some embodiments, the output may be used as a local alert function, and may include an LED, a haptic motor, a buzzer, etc. In some embodiments, the output may be an integral component of the local computer devices 115, 120. Similarly stated, the output may be directly coupled to the processor. For example, the output may be the integral display of a tablet and/or smart phone. In some embodiments, an output module may include, for example, a High Definition Multimedia Interface™ (HDMI) connector, a Video Graphics Array (VGA) connector, a Universal Serial Bus™ (USB) connector, a tip, ring, sleeve (TRS) connector, and/or any other suitable connector operable to couple the local computer devices 115, 120 to the output.

At least one of the sensor units 110 may be operable to transmit physiological data to the local computer devices 115, 120 and/or to the remote computer device 145 continuously, at scheduled intervals, when requested, and/or when certain conditions are satisfied (e.g., during an alarm condition).

The remote computer device 145 may be a computing entity operable to enable a remote user to monitor the output of the sensor units 110. The remote computer device 145 may be functionally and/or structurally similar to the local computer devices 115, 120 and may be operable to receive and/or send signals to at least one of the sensor units 110 via the network 125. The network 125 may be the Internet, an intranet, a personal area network, a local area network (LAN), a wide area network (WAN), a virtual network, a telecommunications network implemented as a wired network and/or wireless network, etc. The remote computer device 145 may receive and/or send signals over the network 125 via communication links 150.

The remote computer device 145 may be used by, for example, a health care professional to monitor the output of the sensor units 110. The remote computer device 145 may receive an indication of physiological data when the sensors detect an alert condition, when the healthcare provider requests the information, at scheduled intervals, and/or at the request of the healthcare provider and/or the person 105.

The server 135 may be configured to communicate with the sensor units 110, the local computer devices 115, 120, third-party sensors 130, the remote computer device 145 and databases 140. The server 135 may perform additional processing on signals received from the sensor units 110, local computer devices 115, 120 or third-party sensors 130, or may simply forward the received information to the remote computer device 145 and databases 140. The databases 140 may be examples of electronic health records ("EHRs") and/or personal health records ("PHRs"), and may be provided by various service providers. The third-party sensor 130 may be a sensor that is not attached to the person 105 but that still provides data that may be useful in connection with the data provided by sensor units 110.

Figure 2:
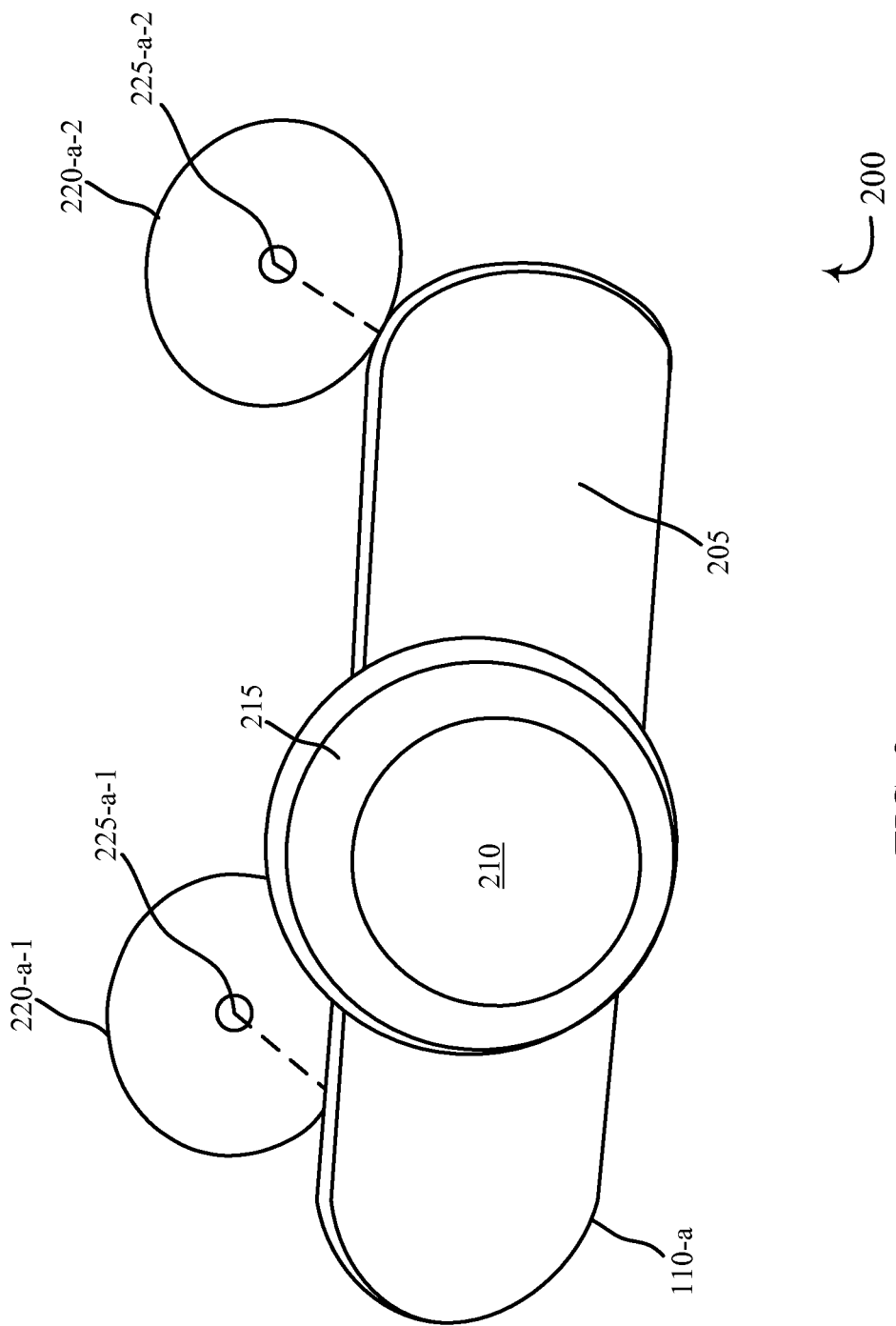
FIG. 2 is a diagram of an example of a physiological sensing device in accordance with various embodiments.

FIG. 2 includes a diagram 200 of an example physiological sensor unit 110-*a*. In diagram 200, sensor unit 110-*a* may be an example of one or more sensor units 110 illustrated in FIG. 1. The sensor unit 110-*a* may include a modular holder or patch, as described in detail below.

The sensing unit 110-*a* may include at least first and second electrodes 220-*a*-1, 220-*a*-2, a holder 205 and an electronics package 210. In the sensor unit 110-*a*, the electrodes 220 and the electronics package 210 may each be removeably coupled to the holder 205. For example, the electrodes 220 and the electronics package 210 may each mechanically couple to the holder 205, such as by snaps, hook and loop fasteners, screw mechanisms, and/or any other suitable means. In the diagram 200, the electrodes 220 may each include a conductive snap 225-*a*-1, 225-*a*-2, which may allow the electrodes 220 to mechanically and electrically couple with the holder 205. The holder 205 may also include an electronics package receptor 215 which may allow the electronics package 210 to mechanically and electrically couple to the holder 205. Each of the electrodes 220, the holder 205 and the electronics package 210 may be removed from each other, if desired, in order to disassemble the sensing unit 110-*a*.

The first and second electrodes 220-*a*-1, 220-*a*-2, the holder 205 and the electronics package 210 may be both electronically and mechanically coupled to each other so as to enable the transmission of various signals through the sensing unit 110-*a*. For example, sensed signals may include electrocardiogram (ECG) signals, impedance drive signals and temperature signals. Each of these may be sensed using the first and second electrodes 220-*a*-1, 220-*a*-2 and then received and processed at the electronics package 210. Alternatively, the signals may be sensed using other active components embedded in the holder. Such components may include, for example, a temperature probe, light emitting devices and light detecting devices. Optical signals may also be transmitted to and from the electronics package 210 and the holder 205 via, for example, optical ports.

In some embodiments, the sensing unit 110-*a* may be a body-worn device. The sensing unit 110-*a* may be coupled to a patient's chest or any other suitable portion of the patient's body, such as the patient's arm or thigh, using an adhesive (e.g., adhesive electrodes 220) or any other suitable mechanism, such as a strap. Alternatively, the sensing unit 110-*a* may be coupled to or integral with a garment configured to be worn by the patient. The garment may be any suitable garment or apparel that can be worn by the patient such as, for example, a belt, a wristband, a headband, an armband, shorts, pants, and/or the like.

In some embodiments, the electrodes 220 may be standard electrodes, such as replaceable electrocardiogram (ECG) electrodes. The electrodes 220 may be designed for a single use. For example, the electrodes 220 may be removed from the holder 205 and discarded after a single use. The electrodes 220 may be hydrogel electrodes and/or may be constructed of conductive fabric or conductive polymer. The electrodes 220 may include an adhesive. In other embodiments, the electrodes 220 may be custom electrodes designed specifically for use with the sensor unit 110-*a*. The electrodes 220 may be 3D—printed to allow patient—or location—customized fit of the electrodes 220 to a patient, and to allow for their use with customized sensing units. For example, hydrogel electrodes may be customized by including hydrogel at optimal locations on the electrodes in order to obtain a best possible signal, based on a patient's morphology.

The holder 205 may also be replaceable and/or designed for a single use. For example, after use, the electronics package 210 may be removed from the holder 205 such that the holder 205 may be discarded. In other embodiments, the holder 205 may be reusable. In yet other embodiments, the holder 205 may be reusable, but may restrict the reuse of the electrodes 220. The holder 205 may be constructed so as to only allow a single use. For example, the holder 205 may be constructed so as to break when disassembled, thereby eliminating multiple use.

The holder 205 may be constructed of polymer, foam, paper, or a non-woven material (e.g., Tyvek™), for example. The holder 205 may include conductive traces and/or wires operable to electrically couple the electrodes 220 to the electronics package 210. The holder 205 may also be operable to determine the distance between and/or relative position of the electrodes 220.

In addition, in some embodiments, the holder 205 may include an antenna (not shown) which may couple to the electronics package 210. As described in further detail herein, the electronics package 210 may be operable to send and/or receive electronic signals (such as GPS signals) via the antenna. The holder 205 may also have an antenna for contactless energy transfer for battery charging while the holder 205 is either being used/worn by a patient or not used or worn. The contactless energy transfer may also allow battery charging while in storage facilities to preserve battery integrity.

In some embodiments, the holder 205 may be stretchable or include a stretchable portion. In such an embodiment, a distance between two electrodes 220 may be changed by stretching the holder 205 or a portion of the holder 205. The holder 205 may include extensions to allow customization to patient morphology or choice of signal locations. For example, the holder 205 may be customized to obtain impedance measurement of respiration from one location or port on the holder 205 or to use different ECG leads in another location or port of the holder 205.

Figure 3:
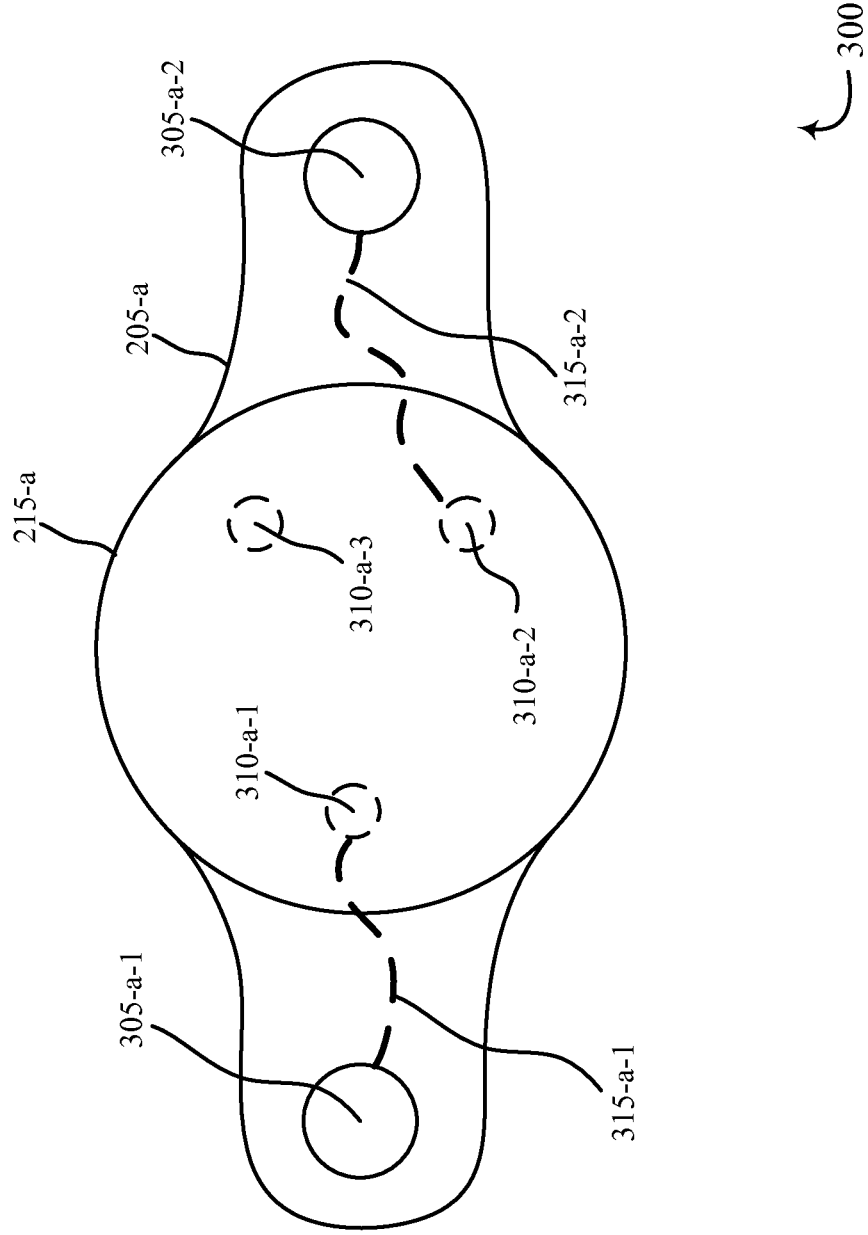
FIG. 3 is a diagram of an example of a holder component of a physiological sensing device in accordance with various embodiments.

The holder 205 may include integral wires and/or conductive traces, as shown in FIG. 3. FIG. 3 illustrates a diagram 300 of a holder 205-a, which may be an example of the holder 205 of FIG. 2. Diagram 300 may illustrate a bottom-view of the holder 205-a, meaning that the side of the holder 205-a that is visible in diagram 300 is the side to which the electrodes 220 (of FIG. 2) may connect. Holder 205-a may include an electronics package receptor 215-a, which may be configured to receive an electronics package (such as electronics package 210 of FIG. 2). Holder 205-a may also include conductive junctions 305-a-1, 305-a-2 to which electrodes 220 (of FIG. 2) may mechanically and electrically couple. The electronics package receptor 215-a may also include conductive attachments 310-a-1, 310-a-2, 310-a-3, such as conductive rivets, located at least on the inside of the electronics package receptor 215-a, which may electrically couple with an inserted electronics package 210 (of FIG. 2). The conductive attachments 310 may be electrically coupled to the conductive junctions 305 via integral wires and/or conductive traces 315. In this way, a signal received through a coupled electrode 220 (of FIG. 2) may travel through the conductive junction 305-a-1, integral wire and/or conductive trace 315-a-1, and conductive rivet 310-a-1 in order to be received by the electronics package 210 (of FIG. 2). Similarly, a signal received through a different coupled electrode 220 may travel through the conductive junction 305-a-2, integral wire and/or conductive trace 315-a-2, and conductive rivet 310-a-2 in order to also be received by the electronics package 210. Therefore, conductive attachments 310-a-1, 310-a-2 may each be configured to transfer signals from electrodes 220 to a connected electronics package 210, while conductive rivet 310-a-3 may be configured as a grounding conductor for a connected electronics package 210. The inclusion of the conductive junctions 305, conductive attachments 310 and integral wires and/or conductive traces 315 in the holder 205-a thus eliminates the need for long external wires running from the electrodes 220 to the electronics package 210. This may be advantageous as external wires can introduce noise into signals detected by the electrodes and can be uncomfortable for the wearer. Additionally, the conductive attachments 310 may also be configured to transmit other signals such as, for example, light.

In an additional embodiment, the holder 205-a may include a unique identification or be uniquely identifiable. The holder 205-a may be mechanically, optically, and/or electically identifiable. Mechanical, optical, or electrical identification of the type of patch may allow for various patch sizes and sensor configurations having the same electronics package 210. Further, any component (for example, the electrodes 220) that is attached to the holder 205-a may also output a signal (for example, a mechanical, optical or electrical signal) which may enable the electronics package 210 to verify that the components are attached.

The holder 205-a may include a storage mechanism to determine a single use is enforced via electrically erasable programmable read-only memory (EEPROM), for example, or other types of storage mechanisms. Alternatively, the holder 205-a may be reusable.

Further, holder 205-a may include a unique serial number such that the electronics package 210 or some other entity or component may determine single patient use and thus reduce patient-to-patient transmitted disease. Each holder 205-a with a unique identifier may enable automatic billing and inventory control by transmitting the unique identifier to a server (for example, server 135 of FIG. 1) where levels may be maintained and reordering may be enabled. Additional embodiments of the sensor units 110 are also described below. For example, FIGS. 4A, 4B, 5, 6, and 7 each illustrate sensor units 110 that include variations of the sensor unit 110-a described above with respect to FIG. 2. For example, components described above with respect to holder 205 may also be integrated into the patches described below with respect to FIGS. 4A, 4B, 5, 6, and 7.

Figure 4A:
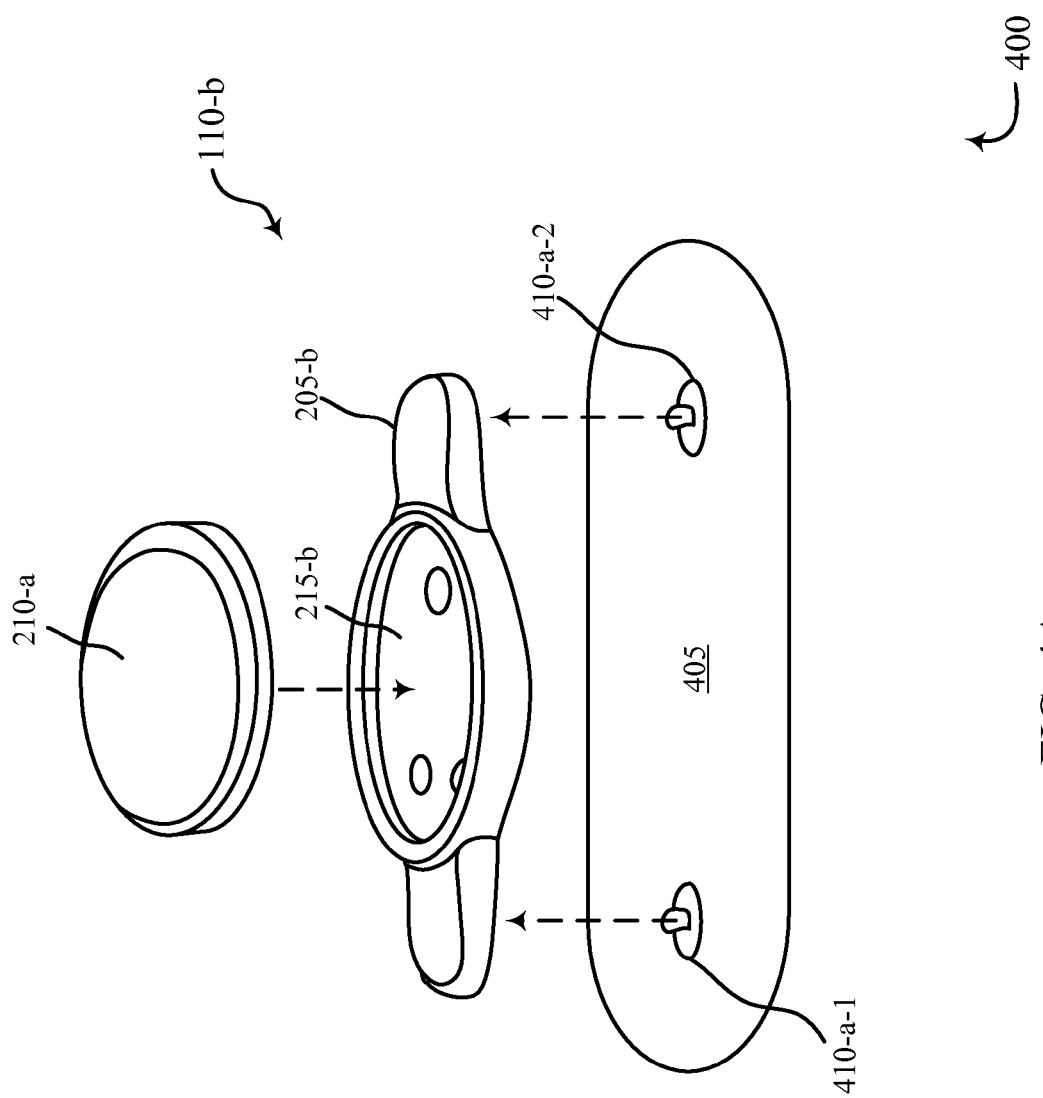
FIGS. 4A and 4B are diagrams of an example of a physiological sensing device in accordance with various embodiments.

FIG. 4A illustrates a diagram 400 of a sensor unit 110-b which may be an example of one or more of the sensor units 110 of FIG. 1. Sensor unit 110-b may include an electronics package 210-a and a holder 205-b, which may also include an electronics package receptor 215-b. The electronics package 210-a, holder 205-b, and electronics package receptor 215-b may each be examples of the electronics package 210, holder 205, and electronics package receptor 215 described above in relation to FIGS. 2 and/or 3. Sensor unit 110-b may also include a patch 405. Patch 405 may replace the first and second electrodes 220-a-1, 220-a-2 of FIG. 2. On a top side of patch 405, conductive attachments 410-a-1, 410-a-2 may mechanically, electrically, or optically couple the patch 405 to the holder 205-b. Other ways may also be used to mechanically and electrically couple the patch 405 to the holder 205-b. For example, the holder 205-b may be attached to the patch 405 using an adhesive, a bonding agent, or even electrostatic charge, for example, while various conductive materials may allow for the electrical coupling of the patch 405 to the holder 205-b. The bottom side of patch 405, which is illustrated by diagram 402 of FIG. 4B, may be at least partially covered by an adhesive, thus allowing the patch 405 to adhere to a patient. The patch 405 may also include or act as first and second electrodes. For example, high profile conductive dry gel 415 may be used on the portions of the bottom side of patch 405 so as to conduct signals received from an attached patient. The high profile conductive dry gel 415 may be used as separate electrodes to electrically couple the patient to electronics package 210-a via the patch 405, the conductive attachments 410, and the holder 205-b. Thus, a first region of high profile conductive dry gel 415-a-1 may be coupled to the conductive snap 410-a-1 (of FIG. 4A), while a second region of high profile conductive dry gel 415-a-2 may be coupled to the conductive snap 410-a-2 (of FIG. 4A). The two regions of high profile conductive dry gel 415-a-1, 415-a-2 may be electrically isolated from each other.

The patch 405 may be constructed of polymer, foam, paper, or a non-woven material (e.g., Tyvek™), for example. The patch 405 may be disposable, meaning that when a patient or practitioner is to change the patch 405, the electronics package 210-a and holder 205-b may be removed from the patch 405, the patch 405 may be disposed of, and a new replacement patch 405 may be coupled to the holder 205-*b* and adhered to the patient. Additionally, the holder 205-*b* may either be disposable or reusable. Thus, when patch 405 is to be removed and replaced, both the patch 405 and the holder 205-*b* may be disposed of and replaced. The electronics package 210-*a* may be removed from the holder 205-*b* prior to the replacement and then re-inserted into a replacement holder 205-*b*.

The patch 405 may also include active components such as temperature sensors or optical components (for example, photodiodes, light emitting diodes, lasers or optical windows) to transmit light bidirectionally between the electronics package 210-*a* and the patient's body.

Figure 4B:
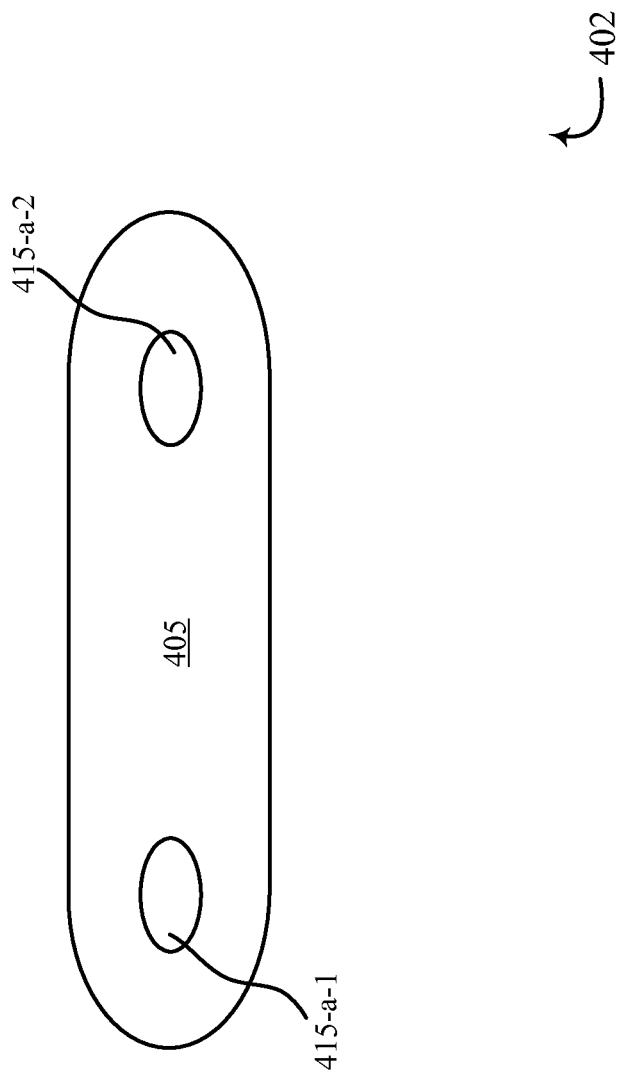
Figure 5:
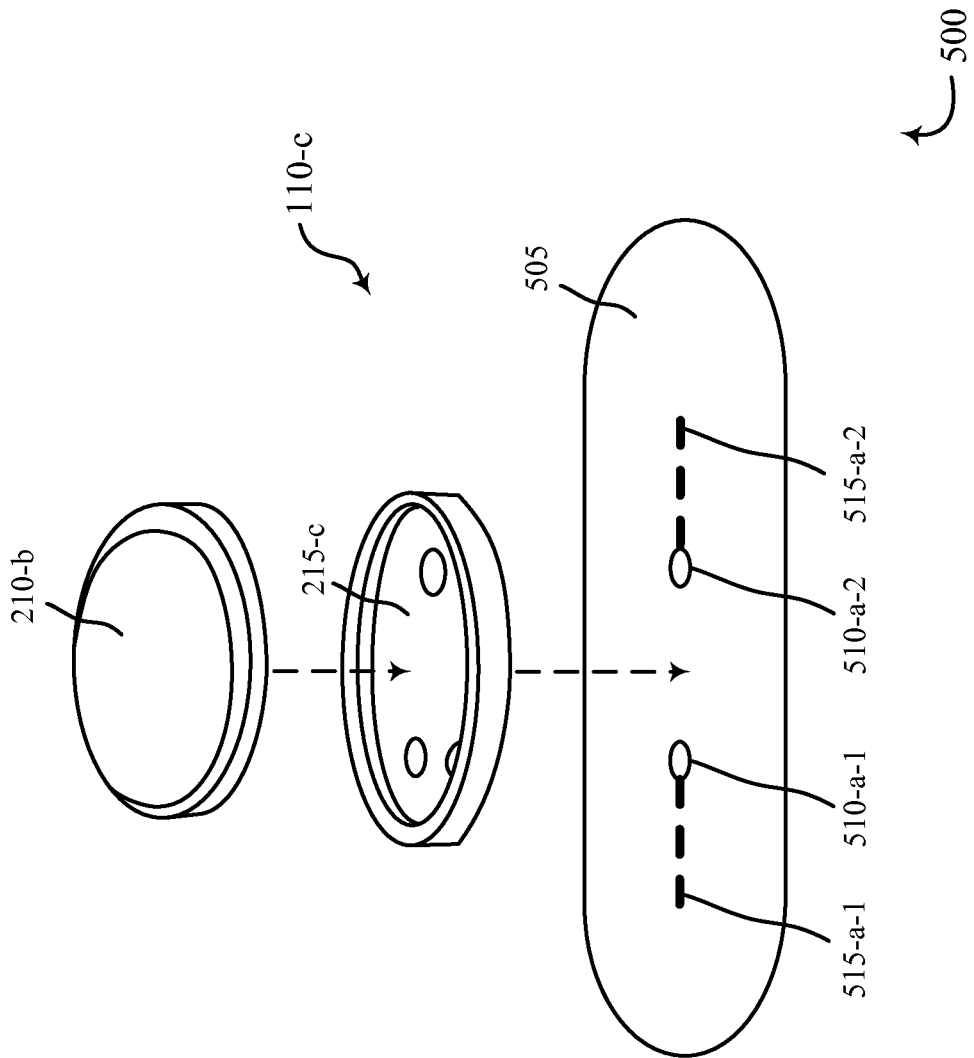
FIG. 5 is a diagram of an example of a physiological sensing device in accordance with various embodiments.

FIG. 5 illustrates a diagram 500 of a sensor unit 110-*c* which may be an example of one or more of the sensor units 110 of FIG. 1. Sensor unit 110-*c* may include an electronics package 210-*b*. However, instead of including a full holder, sensor unit 110-*c* only includes an electronics package receptor 215-*c*. The electronics package 210-*b* and electronics package receptor 215-*c* may each be examples of the electronics package 210 and electronics package receptor 215 described above in relation to FIGS. 2 and/or 3. Sensor unit 110-*c* may also include a patch 505. Patch 505 may be similar to patch 405 of FIG. 4, except that patch 505 is configured to couple directly to the electronics package receptor 215-*c* instead of to a holder. Thus, the top side of patch 505 may include conductive attachments 510-*a*-1, 510-*a*-2, which may electrically couple the patch 505 to the electronics package receptor 215-*c*. The bottom side of patch 505 may be at least partially covered by an adhesive, thus allowing the patch 505 to adhere to a patient. The patch 505 may also include or act as first and second electrodes. For example, high profile conductive dry gel may be used on the portions of the bottom side of patch 505 so as to conduct signals received from an attached patient (as illustrated in FIG. 4B). The high profile conductive dry gel may be used as separate electrodes to electrically couple the patient to electronics package 210-*b* via the patch 505, the conductive attachments 510, and the electronics package receptor 215-*c*. The regions of high profile conductive dry gel may be electrically coupled to the conductive attachments 510 via either embedded or printed conductive tracks 515-*a*-1, 515-*a*-2. The patch 505 may be constructed of polymer, foam, paper, or a non-woven material (e.g., Tyvek™), for example.

In the sensor unit 110-*c*, the electronics package receptor 215-*c* may be permanently attached to the patch 505 via an adhesive. Thus, when a patient or practitioner deems it necessary to replace the patch 505, both the patch 505 and the electronics package receptor 215-*c* are removed and discarded. Meanwhile, the electronics package 210-*b* is removed from the electronics package receptor 215-*c* and may be reused with a replacement electronics package receptor 215-*c* and patch 505.

The patch 505 may include holes, for example, to allow optical and heat transmission between a patient's body and the electronics package 210-*b*.

The exclusion of a holder in sensor unit 110-*c* allows the sensor unit 110-*c* to have a smaller profile, thus adding to the comfort of the patient. Alternatively, the electronics package receptor 215-*c* may be considered as a simplified, low-profile holder.

Figure 6:
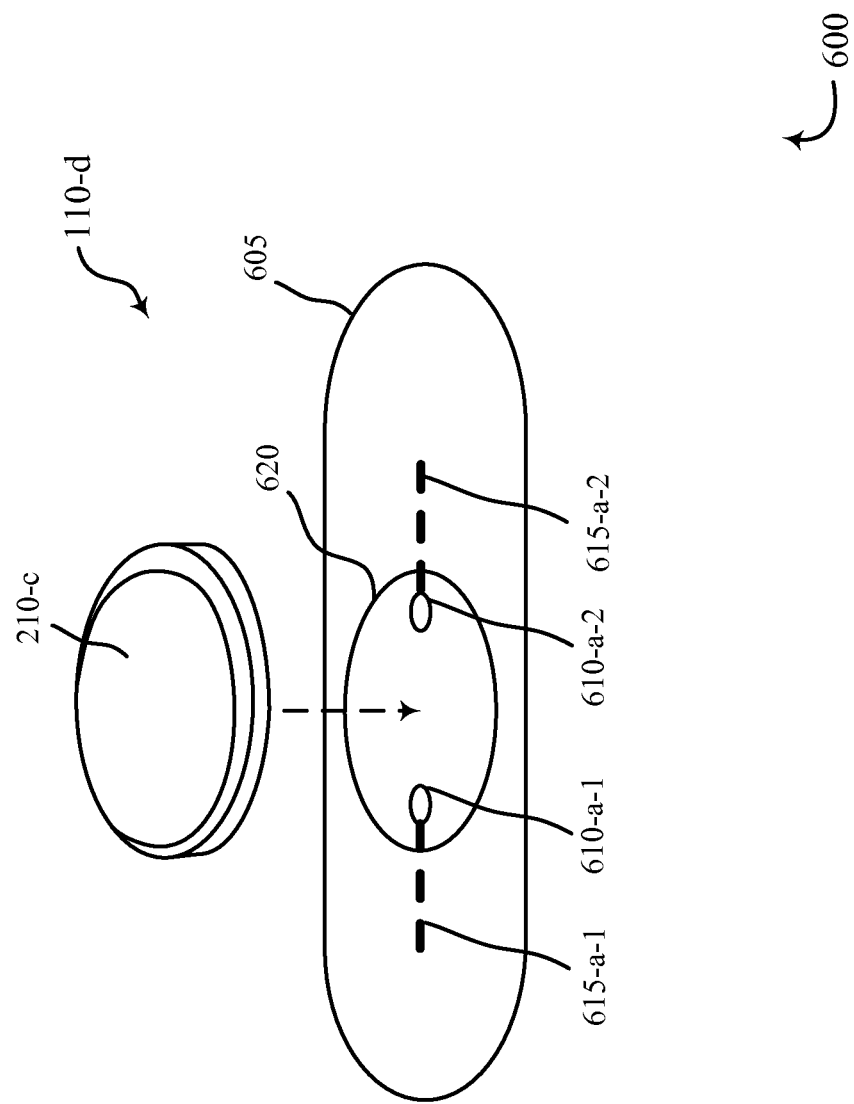
FIG. 6 is a diagram of an example of a physiological sensing device in accordance with various embodiments.

FIG. 6 illustrates a diagram 600 of a sensor unit 110-*d* which may be an example of one or more of the sensor units 110 of FIG. 1. Sensor unit 110-*d* may include an electronics package 210-*c* and a patch 605. The electronics package 210-*c* may be an example of the electronics package 210 described above in relation to FIGS. 2 and/or 3. Patch 605 may be similar to patch 505 of FIG. 5, in that the top side of the patch 605 may include electronically conductive and/or optically transmissive attachments 610-*a*-1, 610-*a*-2, which may electrically, optically, or even thermally couple the patch 605 to the electronics package 210-*c*. The bottom side of patch 605 may be at least partially covered by an adhesive, thus allowing the patch 605 to adhere to a patient. The patch 605 may also include or act as first and second electrodes. For example, high profile conductive dry gel may be used on the portions of the bottom side of patch 605 so as to conduct signals received from an attached patient (as illustrated in FIG. 4B). The high profile conductive dry gel may be used as separate electrodes to electrically couple the patient to electronics package 210-*c* via the patch 605 and the conductive attachments 610. The regions of high profile conductive dry gel may be electrically coupled to the conductive attachments 610 via either embedded or printed conductive tracks 615-*a*-1, 615-*a*-2. The patch 605 may be constructed of polymer, foam, paper, or a non-woven material (e.g., Tyvek™), for example.

In the sensor unit 110-*d*, the electronics package 210-*c* may be temporarily attached to the patch 605 via an adhesive 620. Thus, when a patient or practitioner deems it necessary to replace the patch 605, the electronics package 210-*c* may be removed from the patch 605 and the patch 605 may be discarded. The electronics package 210-*c* may be reattached to a replacement patch 605 using the adhesive 620.

Because sensor unit 110-*d* does not include either a holder or an electronics package receptor, the sensor unit 110-*d* may have an even smaller profile than the sensor units 110-*a*, 110-*b* or 110-*c* described above. Using alternative language, however, the patch 605 may be considered as a simplified, low-profile holder for the electronics package 210-*c*.

Figure 7:
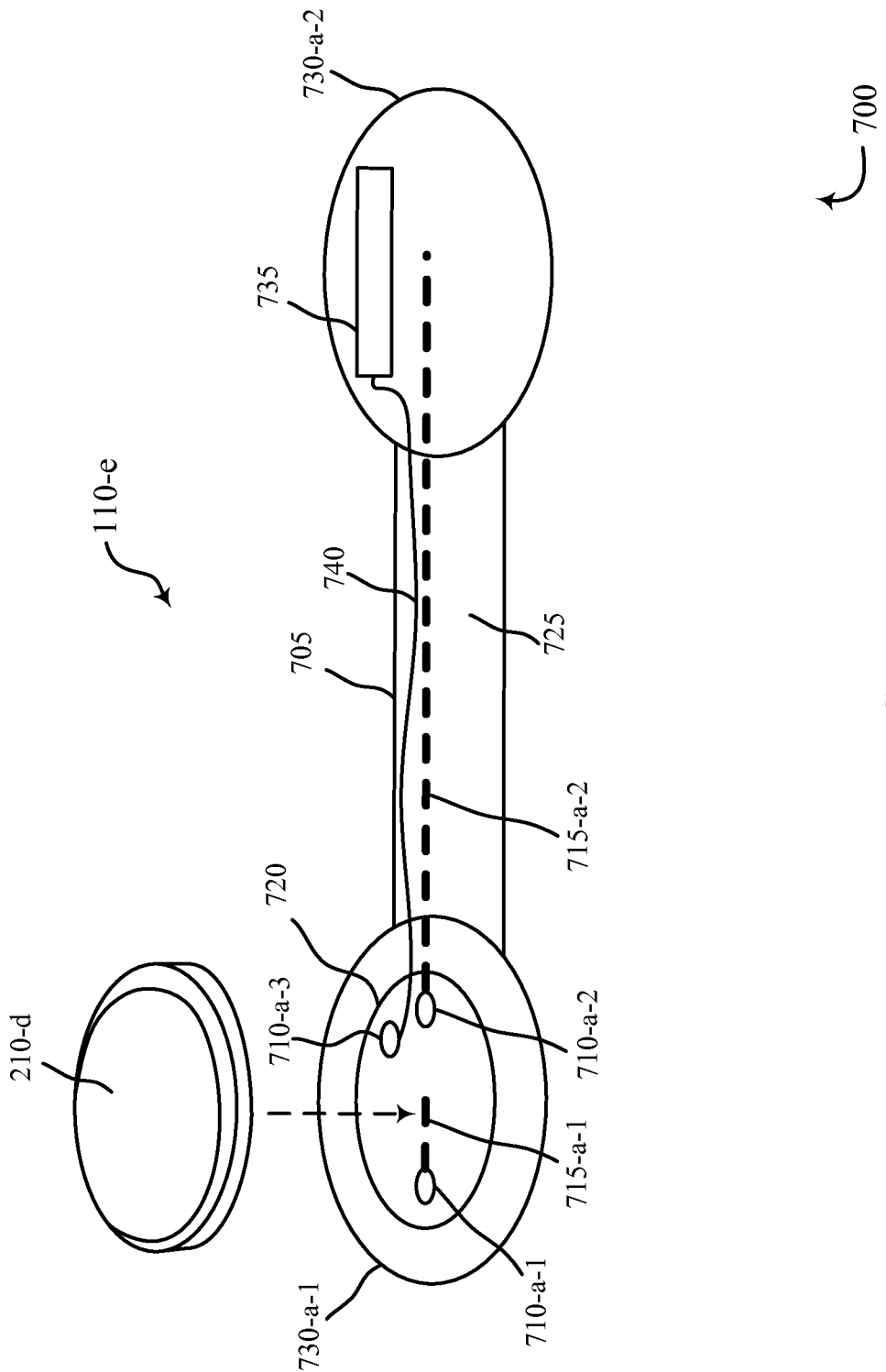
FIG. 7 is a diagram of an example of a physiological sensing device in accordance with various embodiments.

FIG. 7 illustrates a diagram 700 of a sensor unit 110-*e* which may be an example of one or more of the sensor units 110 of FIG. 1. Sensor unit 110-*e* is illustrated to include both an electronics package 210-*d* and a patch 705. However, sensor unit 110-*e* may also include a holder and/or an electronics package receptor similar to those described above in relation to FIG. 2. Thus, in the diagram 700, the electronics package 210-*d* may be temporarily coupled to the patch 705 via an adhesive 720. Alternatively, the electronics package 210-*d* may be coupled to an electronics package receptor such as electronics package receptor 215, which may be permanently attached to the patch 705 using an adhesive (as described in relation to FIG. 5). In yet another alternative, the electronics package 210-*d* may be coupled to an electronics package receptor and holder such as electronics package receptor 215 and holder 205 (of FIG. 2), where the holder may be coupled to the patch 705 using a variety of attachment methods, as described above in relation to FIG. 4.

Patch 705 may be constructed of polymer, foam, paper, or a non-woven material (e.g., Tyvek™), for example. Patch 705 is illustrated as having a top side that may include conductive attachments 710-*a*-1, 710-*a*-2, which may electrically couple the patch 705 to the electronics package 210-*d*. The bottom side of patch 705 may be at least partially covered by an adhesive, thus allowing the patch 705 to adhere to a patient. The patch 705 may also include or act as first and second electrodes. For example, high profile conductive dry gel may be used on the portions of the bottom side of patch 705 so as to conduct signals received from an attached patient (as illustrated in FIG. 4B). The high profile conductive dry gel may be used as separate electrodes to electrically couple the patient to electronics package 210-*d* via the patch 705 and the conductive attachments 710. The regions of high profile conductive dry gel may be electrically coupled to the conductive attachments 710 via either embedded or printed conductive tracks 715-a-1, 715-a-2. The patch 705 may include active components for optical or thermal transmission, and may actively or passively conduct heat or light to the electronics package 210-d. Additionally, the patch 705 may include different sizes, adhesives, etc.

Patch 705 differs from the patches described in relation to FIGS. 4, 5, and/or 6 in that patch 705 includes end regions 730-a-1, 730-a-2 and connecting portion 725. The end regions 730 are designed to be large enough to host or attach to various electronics such as electronics package 210-d. The end regions 730 may also host the electrodes that attach to a patient. The end regions 730 may include the portions of patch 705 that have adhesive for attachment to a patient. The end regions 730 may be connected to each other via the connecting portion 725, which, in an embodiment, may be both long and flexible, allowing the electrodes located at the end regions 730 to be separated from each other by a greater distance than that available through the sensors 110 of FIGS. 2, 4, 5, and/or 6. In an embodiment, the connecting portion 725 may be stretchable. In another embodiment, the connecting portion 725 may have different lengths in order to accommodate various spacing of the end regions 730.

Patch 705 may also include a battery holder 735, which may be included in one of the end regions 730 (for example, end region 730-a-2). Battery holder 735 may accept a replaceable battery or may include a battery that cannot be removed—one that is sealed within the patch 705. Conductive traces 740 may electrically connect the battery holder 735 to the electronics package 210-d via a conductive rivet 710-a-3, for example.

Patch 705 may thus be removed and replaced when a battery housed in its battery holder 735 is drained. The entire patch 705 may be disposable, meaning that the electronics package 210-d may be removed from the patch 705 and affixed to a replacement patch 705 using, for example, the adhesive 720. A battery holder 735 allowing a replaceable battery would enable the patch 705 to continue working for an amount of time while the replaceable battery was swapped. An embedded battery holder 735 would require that the patch 705 be replaced when the battery became exhausted. Due to typical adhesive and skin care of a patient, replacement of the patch 705 in order to replace a battery may also be beneficial to the patient's skin.

Therefore, sensor unit 110-e may have both a low profile and allow for more flexibility in the placement of electrodes via end regions 730. Additionally, sensor 110-e may simplify the removal and reattachment of the sensor 110-e as a result of the patch 705 being disposable and including the battery holder 735. Thus, as the battery is separate from the electronics package 210-d, the electronics package 210-d need not be removed for recharging or replacement of its own battery. Instead, when the battery in battery holder 735 is drained, the electronics package 210-d is simply removed from the patch 705 and inserted or affixed to a replacement patch 705, which may then be reattached to a patient.

Because sensor unit 110-d does not include either a holder or an electronics package receptor, the sensor unit 110-d may have an even smaller profile than the sensor units 110-a, 110-b or 110-c described above. Using alternative language, however, the patch 605 may be considered as a simplified, low-profile holder for the electronics package 210-c.

Figure 8:
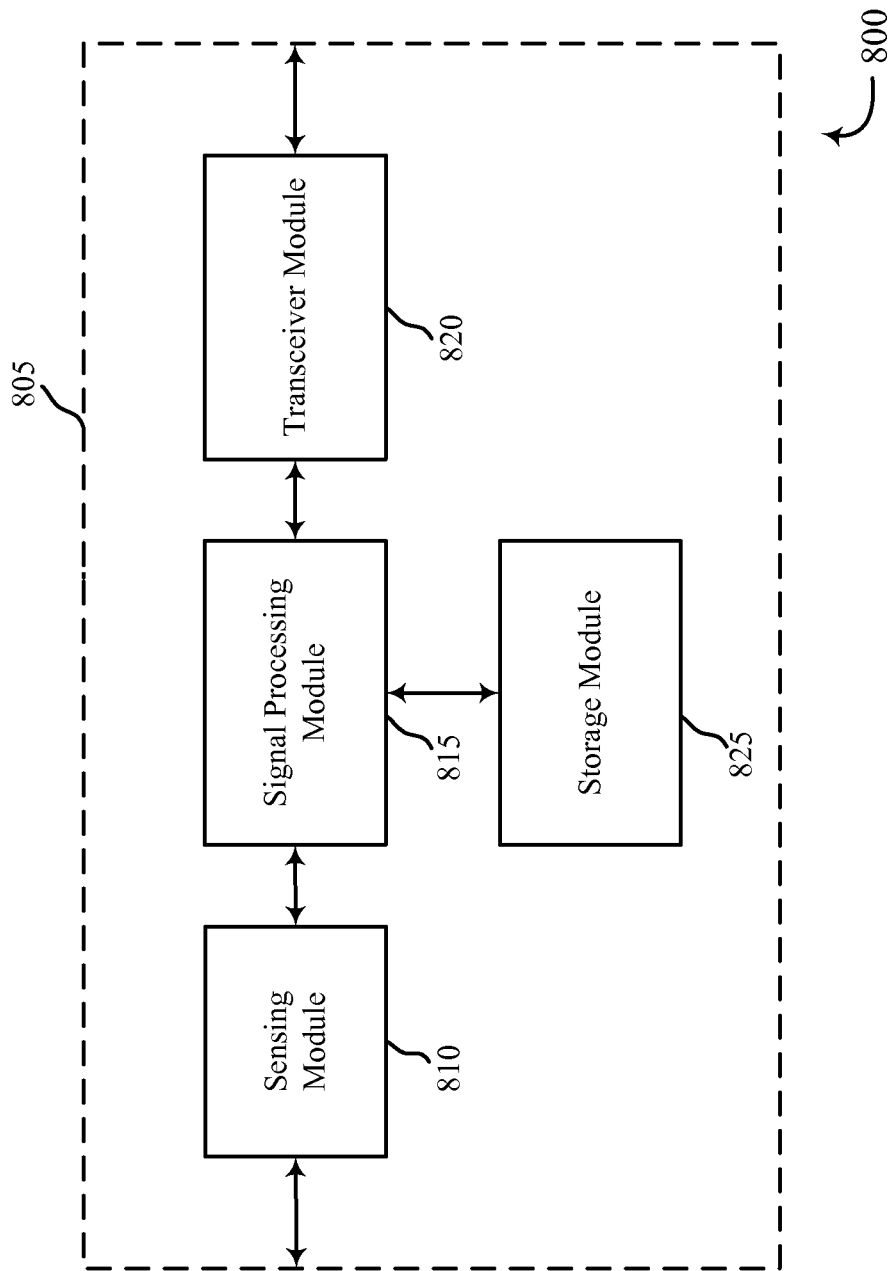
FIG. 8 is a block diagram of an example of a sensor apparatus in accordance with various embodiments.

FIG. 8 is an example of a block diagram 800 of an apparatus 805 that may be used for sensing and reporting physiological parameters, in accordance with various aspects of the present disclosure. In some examples, the apparatus 805 may be an example of aspects of one or more of the sensor units 110 described with reference to FIGS. 1, 2, 4, 5, 6, and/or 7, and may sense and transmit physiological data. The apparatus 805 may also be a processor. The apparatus 805 may include a sensing module 810, a signal processing module 815, a transceiver module 820, and/or a storage module 825. Each of these components may be in communication with each other.

The components of the apparatus 805 may, individually or collectively, be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, Field Programmable Gate Arrays (FPGAs), and other Semi-Custom ICs), which may be programmed in any manner known in the art. The functions of each unit may also be implemented, in whole or in part, with instructions embodied in a memory, formatted to be executed by one or more general or application-specific processors.

In some examples, the sensing module 810 may include at least one sensor. Alternatively, the apparatus 805 may include multiple sensing modules 810, each associated with at least one sensor. For example, a first sensor may be operable to detect a first physiological parameter via a first sensing module. A second sensor may be operable to detect a second physiological parameter via either a second sensing module or the first sensing module. As additional examples, the sensing module 810 can include an accelerometer operable to detect a person's posture and/or activity level. Thus, the sensing module 810 may be operable to determine whether the person is standing, sitting, laying down, and/or engaged in physical activity, such as running The sensing module 810 may also be operable to detect a second physiological parameter. For example, the sensing module 810 may further include an electrocardiogram (ECG) sensing module, a breathing rate sensing module, and/or any other suitable module for monitoring any suitable physiological parameter.

In some examples, the signal processing module 815 includes circuitry, logic, hardware and/or software for processing the signals output by the sensing module 810. The signal processing module 815 may include filters, analog-to-digital converters and other digital signal processing units. Data processed by the signal processing module 815 may be stored in a buffer, for example, in the storage module 825. The storage module 825 may include magnetic, optical or solid-state memory options for storing data processed by the signal processing module 815.

In some examples, the transceiver module 820 may be operable to send and/or receive signals between the sensor units 110 and either the local computer devices 115, 120 or the remote computer device 145 via the network 125 and server 135. In an embodiment, the transceiver module 820 may receive data from other sensor units 110 or apparatuses 805 and may then transmit the data collected from multiple sensor units 110 or apparatuses 805 to either the local computer devices 115, 120 or the remote computer device 145. The transceiver module 820 may include wired and/or wireless connectors. For example, in some embodiments, sensor units 110 can be portions of a wired or wireless sensor network, coupled by the transceiver module 820. The transceiver module 820 may also be a wireless network interface controller ("NIC"), Bluetooth® controller, IR communication controller, ZigBee® controller and/or the like.

Figure 9:
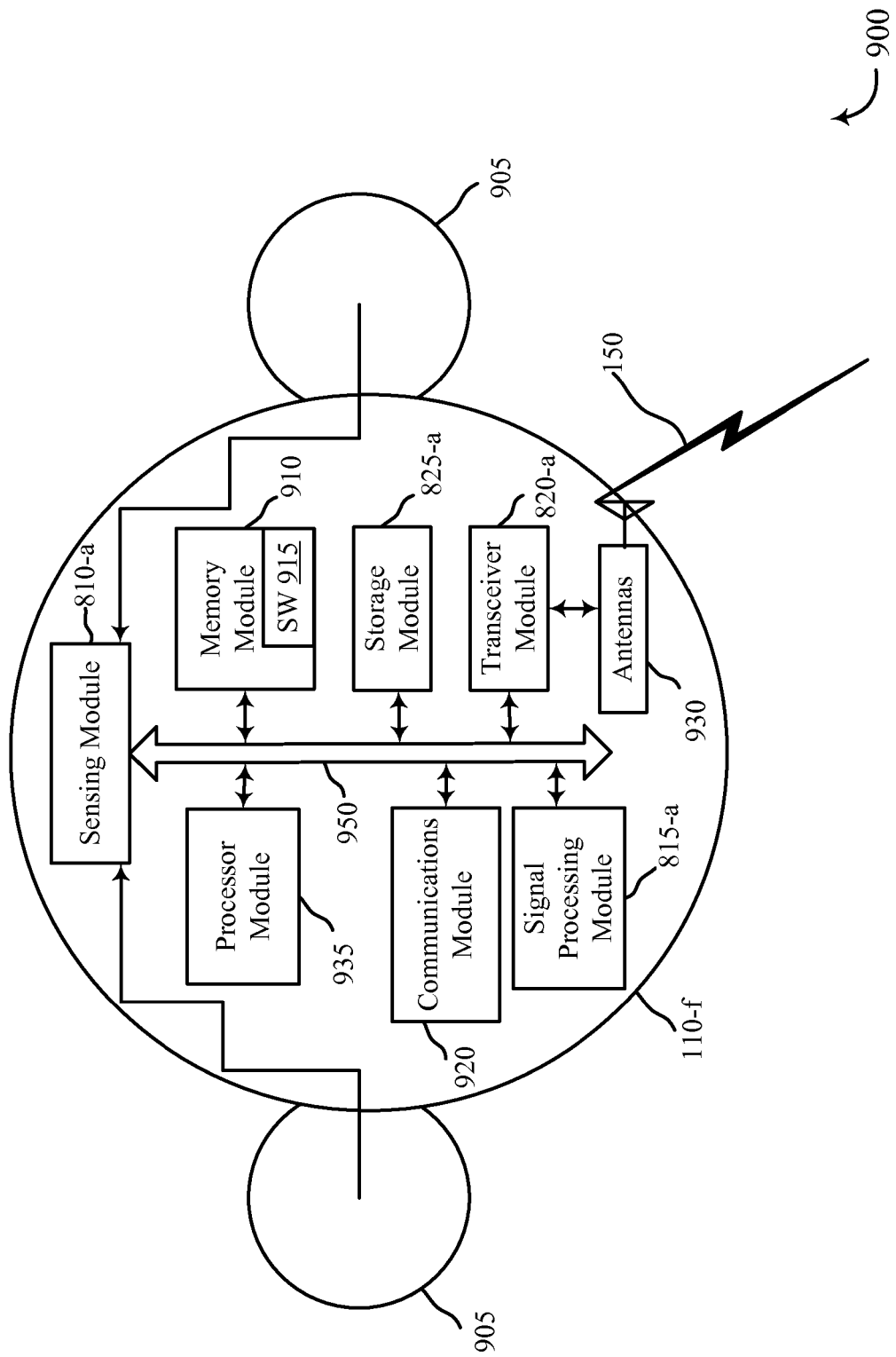
FIG. 9 is a block diagram of an example of a physiological sensing device in accordance with various embodiments.

FIG. 9 shows a block diagram 900 of a sensor unit 110-f for use in remote physiological monitoring, in accordance with various aspects of the present disclosure. The sensor unit 110-*f* may have various configurations. The sensor unit 110-*f* may, in some examples, have an internal power supply (not shown), such as a small battery, to facilitate mobile operation. For example, the internal power supply may be included within an electronics package or with a coupled patch, as described above. Thus, in some examples, the sensor unit 110-*f* may be an example of one or more aspects of one of the sensor units 110 and/or apparatus 805 described with reference to FIGS. 1, 2, 4, 5, 6, 7, and/or 8. The sensor unit 110-*f* may be configured to implement at least some of the features and functions described with reference to FIGS. 1, 2, 4, 5, 6, 7, and/or 8.

The sensor unit 110-*f* may include one or more electrodes 905. The electrodes 905 may be separately attachable to an electronics package via a holder, as in the electrodes 220 of FIG. 2, or may be located on a patch that may be coupled to an electronics package, as in the patches 405, 505, 605, and/or 705 of FIGS. 4, 5, 6, and/or 7. The sensor unit 110-*f* may further include a sensing module 810-a, a processor module 935, a memory module 910, a communications module 920, at least one transceiver module 820-*a*, at least one antenna (represented by antennas 930), a storage module 825-*a*, or a signal processing module 815-*a*. Each of these components may be in communication with each other, directly or indirectly, over one or more buses 950. The sensing module 810-*a*, the storage module 825-*a*, the transceiver module 820-*a*, and/or the signal processing module 815-*a* may be examples of the sensing module 810, the storage module 825, the transceiver module 820 and/or the signal processing module 815, respectively, of FIG. 8.

The memory module 910 may include random access memory (RAM) or read-only memory (ROM). The memory module 910 may store computer-readable, computer-executable software (SW) code 915 containing instructions that are configured to, when executed, cause the processor module 935 to perform various functions described herein for communicating physiological data, for example. Alternatively, the software code 915 may not be directly executable by the processor module 935 but be configured to cause the sensor unit 110-*f* (e.g., when compiled and executed) to perform various of the functions described herein.

The processor module 935 may include an intelligent hardware device, e.g., a CPU, a microcontroller, an ASIC, etc. The processor module 935 may process information received through the transceiver module 820-*a* or information to be sent to the transceiver module 820-*a* for transmission through the antenna 930. The processor module 935 may handle, alone or in connection with the signal processing module 815-*a*, various aspects of signal processing.

The transceiver module 820-*a* may include a modem configured to modulate packets and provide the modulated packets to the antennas 930 for transmission, and to demodulate packets received from the antennas 930. The transceiver module 820-*a* may, in some examples, be implemented as one or more transmitter modules and one or more separate receiver modules. The transceiver module 820-*a* may be configured to communicate bi-directionally, via the antennas 935 and communication link 150, with, for example, local computer devices 115, 120 and/or the remote computer device 145 (via network 125 and server 135 of FIG. 1). Communications through the transceiver module 820-*a* may be coordinated, at least in part, by the communications module 920. While the sensor unit 110-*f* may include a single antenna, there may be examples in which the sensor unit 110-*f* may include multiple antennas 930.

As examples, the transceiver module 820-*a* may include a Bluetooth® module, an IEEE 802.15.4 module with custom stack, a ZigBee module, a wireless network interface controller (NIC), a cellular telephone module, and/or any other suitable module configured to send signals. The transceiver module 820-*a* may be operable to send a signal, for example over a network, the Internet, a cellular telephone link, and/or any other suitable communication means. In some embodiments, the transceiver module 820-*a* may include a short-range transmitter, for example, having a range of less than approximately 1000 feet.

The signal processing module 815-*a* may be used to interpret and process signals received from the electrodes 905 via the sensing module 810-*a*. Using the received signals, the signal processing module 815-*a* may calculate physiological parameters, such as heart rate, respiratory rate, and so forth.

The sensor unit 110-*f* may be operable to generate alerts, such as an audible alert, a visual alert, a haptic alert, and/or any other suitable type of alert. The sensor unit 110-*f* may generate an alert when, for example, a module of the sensor unit 110-*f* determines that a vital sign of a wearer has exceeded a threshold. For example, the electrodes 905 and sensing module 810-*a* may detect an electrical signal associated with a heart rate of the wearer which the signal processing module 815-*a* may process and compare to a threshold such that if the wearer's heart rate rises above a predetermined level and/or falls below a predetermined level, the sensor unit 110-*f* may generate an alert.

The sensing module 810-*a* may include sensors such as accelerometers, gyroscopes, GPS modules, and so forth and may be operable to act as a pedometer, detect activity level, determine burned calories, and so forth. The collected data may be stored in the storage module 825-*a*, for example.

The sensing module 810-*a* of sensor unit 110-*f* may be further illustrated and described in U.S. patent application Ser. No. 13/087,540, filed Apr. 15, 2011 and published as U.S. Publication No. 2011/0257542; U.S. patent application Ser. No. 13/154,317, filed Jun. 6, 2011 and published as U.S. Publication No. 2012/0143019; U.S. patent application Ser. No. 12/318,026, filed Dec. 19, 2008 and published as U.S. Publication No. 2009/0227856; U.S. Pat. No. 8,400,302, issued Mar. 19, 2013; U.S. patent application Ser. No. 12/311,276, filed Sep. 21, 2007 and published as U.S. Patent Application No. 2009/0281394; U.S. Pat. No. 8,079,247, issued Dec. 20, 2011; U.S. patent application Ser. No. 13/361,633, filed Jan. 30, 2012 and published as U.S. Publication No. 2013/0144130; U.S. patent application Ser. No. 14/279,051, filed May 15, 2014; and/or U.S. patent application Ser. No. 14/279,003, filed May 15, 2014, each of which is commonly owned and is incorporated herein by reference in its entirety.

Figure 10:
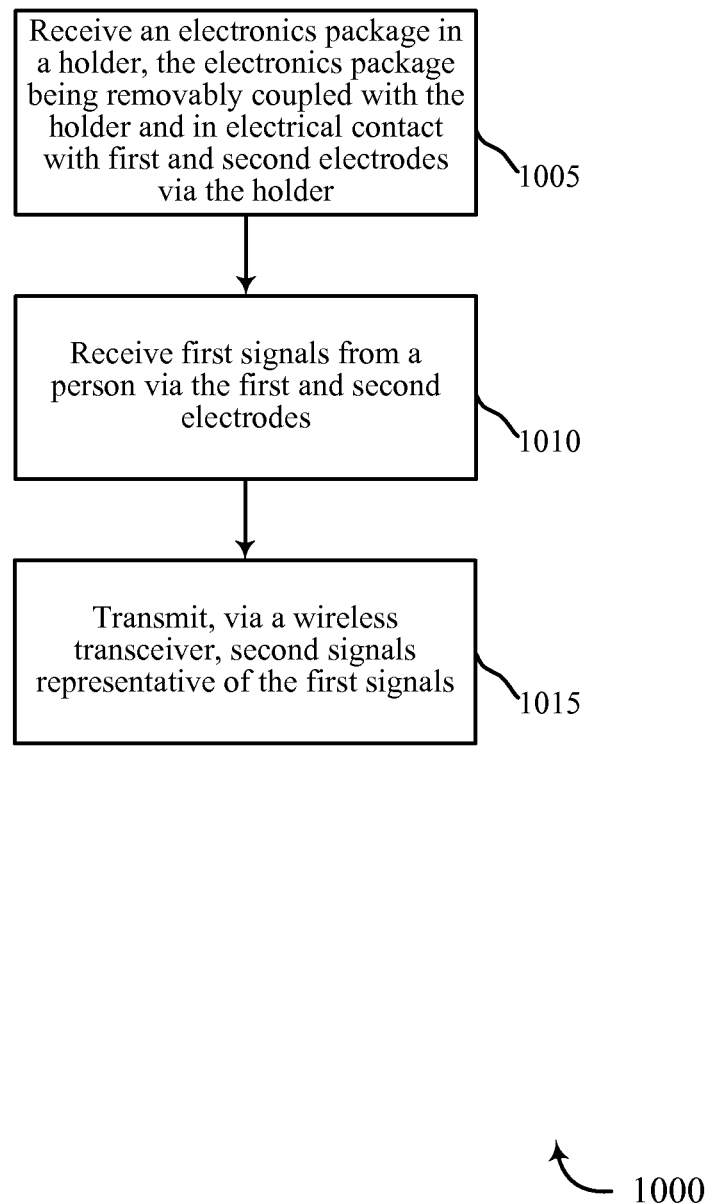
FIG. 10 is a flowchart of a method for remote monitoring of a person, in accordance with various embodiments.

FIG. 10 is a flow chart illustrating an example of a method 1000 for remote monitoring of a person, in accordance with various aspects of the present disclosure. For clarity, the method 1000 is described below with reference to aspects of one or more of the sensor units 110 described with reference to FIGS. 1, 2, 4, 5, 6, 7 and/or 9, respectively, or aspects of one or more of the apparatus 805 described with reference to FIG. 8. In some examples, a sensor unit such as one of the sensor units 110 or an apparatus such as one of the apparatuses 805 may execute one or more sets of codes to control the functional elements of the sensor unit or apparatus to perform the functions described below.

At block 1005, the method 1000 may include receiving an electronics package in a holder, the electronics package being removably coupled with the holder and in electrical contact with first and second electrodes via the holder. The first and second electrodes may be separately coupled to the holder and electronics package (as described above with respect to FIG. 2) or may be part of a patch (as described above with respect to FIGS. 4, 5, 6, and/or 7). The holder may be a component that receives the electronics package, as described above with reference to the holder 205 (of FIGS. 2, 3, and/or 4), the electronics package receptor 215 (of FIGS. 2, 3, 4, and/or 5), or the patches 605, 705 (of FIGS. 6 and/or 7).

At block 1010, the method 1000 may include receiving first signals from a person via the first and second electrodes. The first and second electrodes may receive signals from a patient, for example. The first signals may be processed by one or both of a sensing module (such as sensing module 810 of FIGS. 8 and/or 9) and a signal processing module (such as signal processing module 815 of FIGS. 8 and/or 9). The signal processing module may convert the sensed first signals into electrical signals that may be transmitted from the sensor unit. Thus, at block 1015, the method 1000 may include transmitting, via a wireless transceiver, second signals representative of the first signals.

In some embodiments, the operations at blocks 1005, 1010, or 1015 may be performed using the sensor units 110 and/or apparatus 805 described with reference to FIGS. 1, 2, 3, 4, 5, 6, 7, 8, and/or 9. Nevertheless, it should be noted that the method 1000 is just one implementation and that the operations of the method 1000 may be rearranged or otherwise modified such that other implementations are possible.

While various embodiments have been described above, it should be understood that they have been presented by way of example only, and not limitation. For example, although FIG. 7 has been described with reference to including a battery holder 735 that may hold a battery that may be disposed with patch 705, a battery included in battery holder 735 may also be removed and replaced or recharged. In some embodiments, conductive traces of the patch 705 may be operable to couple the battery holder 735 to a battery charger (e.g. electrical contacts of the patch 705 may contact a battery charger). In other embodiments, the battery may be charged through non-contact means, such as inductive charging (e.g., utilizing an antenna of the sensor unit (as included in either the electronics package or the patch/holder). In yet another embodiment, the electronics package 210 itself may include a battery and may be decoupled from a patch or holder before being physically and electrically coupled to a battery charger.

Additionally, although the sensor unit 110 has been illustrated and described as having two electrodes 220, 905, in other embodiments, the sensor unit 110 may include any number of electrodes, such as, for example, one electrode, three electrodes, five electrodes or ten electrodes. In this manner, the electronics package 210 may couple to any number of electrodes in any of the manners described herein.

Where schematics and/or embodiments described above indicate certain components arranged in certain orientations or positions, the arrangement of components may be modified. While the embodiments have been particularly shown and described, it will be understood that various changes in form and details may be made.

The above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in an order different from that described, and various steps may be added, omitted, or combined. Also, features described with respect to certain embodiments may be combined in other embodiments.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration. A processor may in some cases be in electronic communication with a memory, where the memory stores instructions that are executable by the processor.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items indicates a disjunctive list such that, for example, a list of "at least one of A, B, or C" means A or B or C or AB or AC or BC or ABC (i.e., A and B and C).

A computer program product or computer-readable medium both include a computer-readable storage medium and communication medium, including any mediums that facilitates transfer of a computer program from one place to another. A storage medium may be any medium that can be accessed by a general purpose or special purpose computer. By way of example, and not limitation, computer-readable medium can comprise RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote light source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. A remote physiological sensing device, comprising:
   a patch including first and second electrodes located at opposite ends of the patch and including a flexible connecting member located between the first and second electrodes; and
   an electronics package comprising an adhesive by which the electronics package is removably coupled with the patch, and wherein the electronics package is in electrical contact with the first and second electrodes via the patch, the electronics package including a housing, a wireless transceiver and electronic circuitry configured to process signals received via the first and second electrodes and the wireless transceiver, the electronics package coupled to the patch proximate to the first electrode such that the electronics package is separated from the second electrode by the flexible connecting member.

2. The device of claim 1, the patch further comprising conductive traces to electrically couple each of the first and second electrodes with the electronics package.

3. The device of claim 1, further comprising a battery included within the patch.

4. The device of claim 3, wherein the battery is sealed within the patch.

5. The device of claim 1, further comprising:
   a battery located in the patch,
   wherein the battery is proximate to the first electrode and the electronics package is proximate to the second electrode.

6. The device of claim 5, the patch further comprising a connecting member between the electronics package and the battery through which the battery is electrically coupled to the electronics package.

7. The device of claim 6, the connecting member further comprising at least a portion that is stretchable.

8. The device of claim 1, further comprising a holder to which the electronics package is removably coupled, the holder being coupled to the patch.

9. The device of claim 8, wherein the holder is removably coupled to the patch.

10. The device of claim 1, further comprising an optical coupling between the patch and the electronics package.

11. The device of claim 1, the patch further comprises a unique identifier.

12. The device of claim 1, the patch further comprising at least a portion that is made of foam.

13. The device of claim 1, further comprising a battery included within the electronics package.

14. The device of claim 1, further comprising a battery that is sealed within the patch.

15. The device of claim 1, wherein the patch includes single-use electrodes.

16. The device of claim 1, the patch further comprising an adhesive layer for attachment to a person.

17. A method for remote monitoring of a person, the method comprising:
   receiving an electronics package at a patch, the electronics package comprising an adhesive by which the electronics package is removably coupled with the patch, and wherein the electronics package is in electrical contact with first and second electrodes located at opposite ends of the patch, the patch including a flexible connecting member located between the first and second electrodes, the electronics package being received at the patch proximate to the first electrode such that the electronics package is separated from the second electrode by the flexible connecting member;
   receiving first signals from a person via the first and second electrodes; and
   transmitting, via a wireless transceiver, second signals representative of the first signals.

18. The method of claim 17, further comprising:
   releasing the electronics package from the patch based on a battery located in the patch being drained.

19. A remote physiological sensing device, comprising:
   means for receiving an electronics package at a patch, the electronics package comprising an adhesive by which the electronics package is removably coupled with the patch, and wherein the electronics package is in electrical contact with first and second electrodes located at opposite ends of the patch, the patch including a flexible connecting member located between the first and second electrodes, the electronics package being received at the patch proximate to the first electrode such that the electronics package is separated from the second electrode by the flexible connecting member;
   means for receiving first signals from a person via the first and second electrodes; and
   means for transmitting, via a wireless transceiver, second signals representative of the first signals.

20. The device of claim 19, further comprising:
   means for releasing the electronics package from the patch based on a battery located in the patch being drained.

* * * * *